(12) United States Patent
Gustavson et al.

(10) Patent No.: US 7,050,694 B2
(45) Date of Patent: May 23, 2006

(54) CONTINUOUSLY VARIABLE ATTENUATION OF AN OPTICAL SIGNAL USING AN OPTICAL ISOLATOR

(75) Inventors: Todd L. Gustavson, Sunnyvale, CA (US); Konstantinos G. Haritos, Saratoga, CA (US); Subra Nagarajan, Livermore, CA (US); Ramesh Sundaram, Fremont, CA (US)

(73) Assignee: Finisar Corporation, Sunnyvale, CA (US)

( * ) Notice: Subject to any disclaimer, the term of this patent is extended or adjusted under 35 U.S.C. 154(b) by 182 days.

(21) Appl. No.: 10/426,453

(22) Filed: Apr. 29, 2003

(65) Prior Publication Data

US 2004/0086256 A1    May 6, 2004

Related U.S. Application Data

(60) Provisional application No. 60/422,396, filed on Oct. 30, 2002.

(51) Int. Cl.
*G02B 6/00* (2006.01)
(52) U.S. Cl. ........................... 385/140; 385/134
(58) Field of Classification Search ............... 385/140, 385/134
See application file for complete search history.

(56) References Cited

U.S. PATENT DOCUMENTS

| | | | | |
|---|---|---|---|---|
| 5,076,675 A | * | 12/1991 | Kusaka et al. | 359/484 |
| 5,204,868 A | * | 4/1993 | Konno et al. | 372/34 |
| 5,978,535 A | * | 11/1999 | Mitsuda et al. | 385/88 |
| 6,297,901 B1 | | 10/2001 | Kim | |
| 6,384,957 B1 | | 5/2002 | Ikeda et al. | |

\* cited by examiner

*Primary Examiner*—Jennifer Doan
(74) *Attorney, Agent, or Firm*—Workman Nydegger

(57) ABSTRACT

Method and apparatus of attenuating an optical signal without adding extra components is presented. The drive current of the optical signal source is set to meet a predetermined bandwidth requirement and exceed a predetermined amplitude requirement. An optical isolator that is used to prevent back-reflections from reaching the optical signal source is used to achieve the desired amount of attenuation. More specifically, the invention includes controlling the attenuation by tuning an angle $\theta$ between the transmission axis of a polarizer that is part of the optical isolator and the original polarization state of the optical signal. By increasing the angle $\theta$, the amount of attenuation is increased; by decreasing the angle $\theta$, the amount of attenuation is decreased. The invention allows continuous tuning of the angle $\theta$.

19 Claims, 4 Drawing Sheets

CONTINUOUSLY VARIABLE ATTENUATION OF AN OPTICAL SIGNAL USING AN OPTICAL ISOLATOR

RELATED APPLICATION

This patent application claims the benefit, under 35 U.S.C. § 119(e), of U.S. Provisional Application No. 60/422,396 filed on Oct. 30, 2002, which is incorporated herein in its entirety.

FIELD OF THE INVENTION

The present invention relates generally to optical transmitters, and more particularly to the attenuation of optical signals.

BACKGROUND OF THE INVENTION

Transmitter Optical Sub-Assemblies (TOSAs) are well known in the art of optical networks. A TOSA operates as an electro-optical converter for use in data communications and telecommunications applications. It transforms electrical signals into corresponding optical signals that are then focused into an optical fiber. Once the optical signal reaches its destination, it is typically focused into a ROSA (Receiver Optical Sub-Assembly) for conversion back into a corresponding electrical signal.

A TOSA typically includes a diode laser for producing an optical signal and a lens for focusing the optical signal into the input end of an optical fiber. Diode lasers (e.g. distributed feed-back diode lasers) are typically sensitive to back reflected light (e.g. light reflected off of the input face of the optical fiber back into the diode laser). Therefore, TOSAs also typically include an optical isolator located between the laser and the optical fiber that allows light to pass from the diode laser to the optical fiber while preventing any back-reflected light from reaching the diode laser.

A common optical isolator is a Faraday rotator device having an input linear polarizer, a garnet crystal and an output linear polarizer. Normally, the transmission axis of the input linear polarizer is aligned to the linear polarization of the diode laser output to maximize light transmission through the input linear polarizer. The garnet crystal is subjected to a saturating magnetic field, making it a Faraday rotator having a thickness chosen such that the polarization of transmitted light is rotated by approximately 45 degrees. The polarization is rotated in the same direction regardless of the propagation direction of the light. The transmission axis of the output linear polarizer is oriented at approximately 45 degrees relative to that of the input linear polarizer to maximize the transmission of the light from the diode laser that has passed through the input polarizer and Faraday rotator.

Any light that is reflected back toward the diode laser is first incident upon the output polarizer, which passes only light linearly polarized along its axis. The polarization of this admitted light is rotated by approximately 45 degrees by the garnet crystal, and ends up being orthogonal to the transmission axis of the input polarizer. At the input polarizer, this light that is polarized orthogonal to the transmission axis is either absorbed or reflected away from the fiber. Optical isolators are used extensively and have excellent performance with typical insertion loss of <0.3 dB and isolation of >25 dB (reduction factor for reflected light).

TOSAs must satisfy certain bandwidth and power requirements in order to function properly for use in practical networking applications. These characteristics both vary as a function of the electrical current through the diode laser. Therefore, many times it is not possible to satisfy both the power requirement as well as the bandwidth requirement simply by adjusting the diode laser current. One solution is to set the diode laser current to meet the bandwidth requirement even though it may possibly exceed the power requirement, and then attenuate the diode laser output as needed to then meet the power requirement. A prior method of achieving this attenuation is to insert an optical plate with an attenuating thin-film coating, or to use a neutral density filter to attenuate the optical power. Such an optical filter has been used with an optical isolator (see for example U.S. Pat. No. 6,297,901). Adding additional optical element(s), however, is disadvantageous because of the cost of the optical element(s), the creation of additional optical interfaces, and the increased possibility of a failure related to the added optical element(s) (e.g. coating failure, mechanical mounting failure, alignment failure, surface contamination, etc.). Additionally, the attenuation of the added passive optical element(s) is not adjustable, thus requiring a series of optical elements to be created and stocked.

A variety of active devices have also been used to achieve variable attenuation. For example, it is possible to vary the magnetic field applied to the Faraday rotator to adjust the rotation angle of the light relative to the output polarizer (see for example U.S. Pat. No. 6,384,957). However, this solution increases the complexity and cost of the TOSA, and decreases the effectiveness of the optical isolator in completely blocking back-reflected light.

There is a need for a simple, inexpensive way to achieve arbitrary and continuously adjustable attenuation values for laser light focused into an optical fiber, without adding to the cost or complexity of the TOSA.

SUMMARY OF THE INVENTION

The invention solves the aforementioned problems by providing a continuously adjustable attenuation by using the optical isolator itself, without compromising its ability to block back-reflected light. The variable optical attenuation device of the invention includes an optical signal source generating an optical signal that is polarized in an original polarization direction D, an optical isolator that receives the optical signal and transmits only light that is substantially polarized in a polarizer direction $T_1$, and a means for rotating at least one of the optical isolator and the optical signal source to adjust an angle θ, which is the angle between the original polarization direction D and the polarizer direction $T_1$.

The attenuation method of the invention includes tuning the angle θ. By increasing the angle θ, a greater attenuation is achieved because a smaller portion of the original optical signal is transmitted. By decreasing the angle θ, the amount of attenuation that is achieved can be decreased, increasing the signal intensity.

Other objects and features of the present invention will become apparent by a review of the specification, claims and appended figures.

DETAILED DESCRIPTION OF THE PREFERRED EMBODIMENTS

The invention is a method and device for attenuating the output of an optical signal source (e.g., a diode laser) without extra components.

Figure 1:
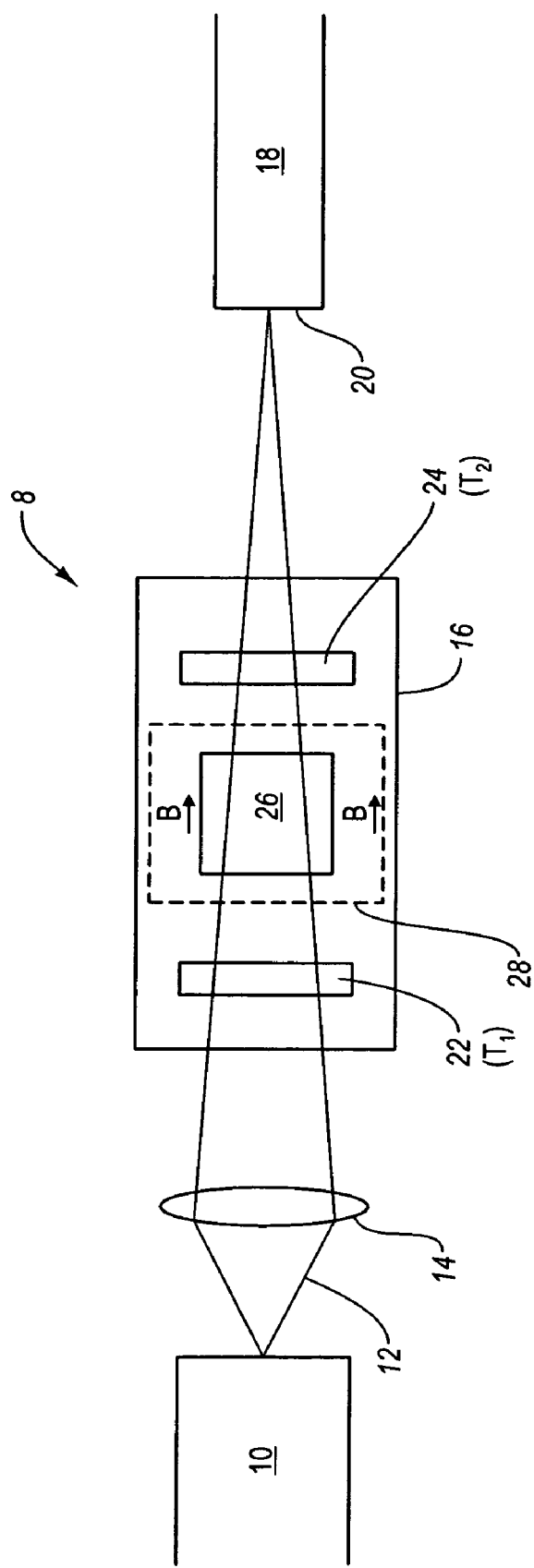
FIG. 1 is a cross sectional view of an optical signal source and an optical isolator that are combined for the present invention.

FIG. 1 depicts an embodiment of a variable optical attenuation device 8 that includes a diode laser 10 that produces a diverging optical beam 12, one or more lens elements 14, an optical isolator 16 and an optical fiber 18. The optical fiber 18 may or may not be a part of the TOSA device. The lens element 14 focuses the optical beam 12 from the diode laser into the input end 20 of the optical fiber. Depending upon the type of diode laser and optical fiber used, lens element 14 could be a single optical element as shown in FIG. 1, or multiple optical elements placed before and/or after the optical isolator 16.

The optical isolator 16 further includes an input linear polarizer 22, an output linear polarizer 24, an optical element (such as a garnet) 26 disposed between the polarizers 22, 24, and a magnetic field source (such as a static magnet) 28 for immersing the garnet 26 in a magnetic field B. The garnet and magnetic field are set to rotate the polarization of light traversing therethrough by 45 degrees in one direction regardless of whether the light is traveling toward or away from the diode laser 10 (e.g. in the direction shown by the arrow A in FIG. 2). The transmission axis $T_2$ of the output linear polarizer 24 is fixed at a predetermined orientation relative to the transmission axis $T_1$ of the input linear polarizer 22. The optical element 26 is an asymmetric polarization rotator, such as a Faraday rotator.

The optical beam 12 from laser diode 10 is generally linearly polarized in a direction D. To align the optical isolator for minimum attenuation of the forward traveling light while blocking the back-reflected light, the transmission axis $T_1$ of the input linear polarizer 22 is aligned with the polarization direction D of the optical beam 12 from diode laser 10 to maximize the transmission of the optical beam 12 through polarizer 22. The garnet crystal 26, immersed in magnetic field B, rotates the polarization of optical beam 12 by a predetermined angle that matches the orientation of $T_2$ relative to $T_1$. Thus, after passing through the garnet crystal 26, the polarization direction of optical beam 12 is aligned with transmission axis $T_2$. Substantially all of the optical beam 12 is transmitted through output polarizer 24. Preferably, the transmission axis $T_2$ is oriented at approximately 45° angle relative to the transmission axis $T_1$ and the garnet crystal 26 rotates a light beam propagating through it by approximately 45°. The invention is described herein in the context of this preferred embodiment.

Once the optical beam 12 exits the optical isolator 16, it is incident upon, and is coupled into, the input end 20 of optical fiber 18. A small amount of the optical beam 12 entering optical fiber 18 may be reflected back toward the optical isolator 16 either by fiber input end 20 or other optical components at either end of optical fiber 18. The output optical polarizer 24 transmits only that portion of this back-reflected light that is aligned with transmission axis $T_2$. The transmitted back-reflected light then undergoes a 45 degree polarization rotation by the garnet 26 in the same direction that the optical beam 12 was rotated while propagating toward the optical fiber 18. Having experienced two sets of 45-degree rotations in the same direction, the back-reflected light now has a polarization state that is orthogonal to the transmission axis $T_1$. Therefore, the input polarizer 22 generally absorbs or reflects away all of the back reflected light incident thereon, preventing the back-reflected light from reaching the diode laser 10.

Figure 2:
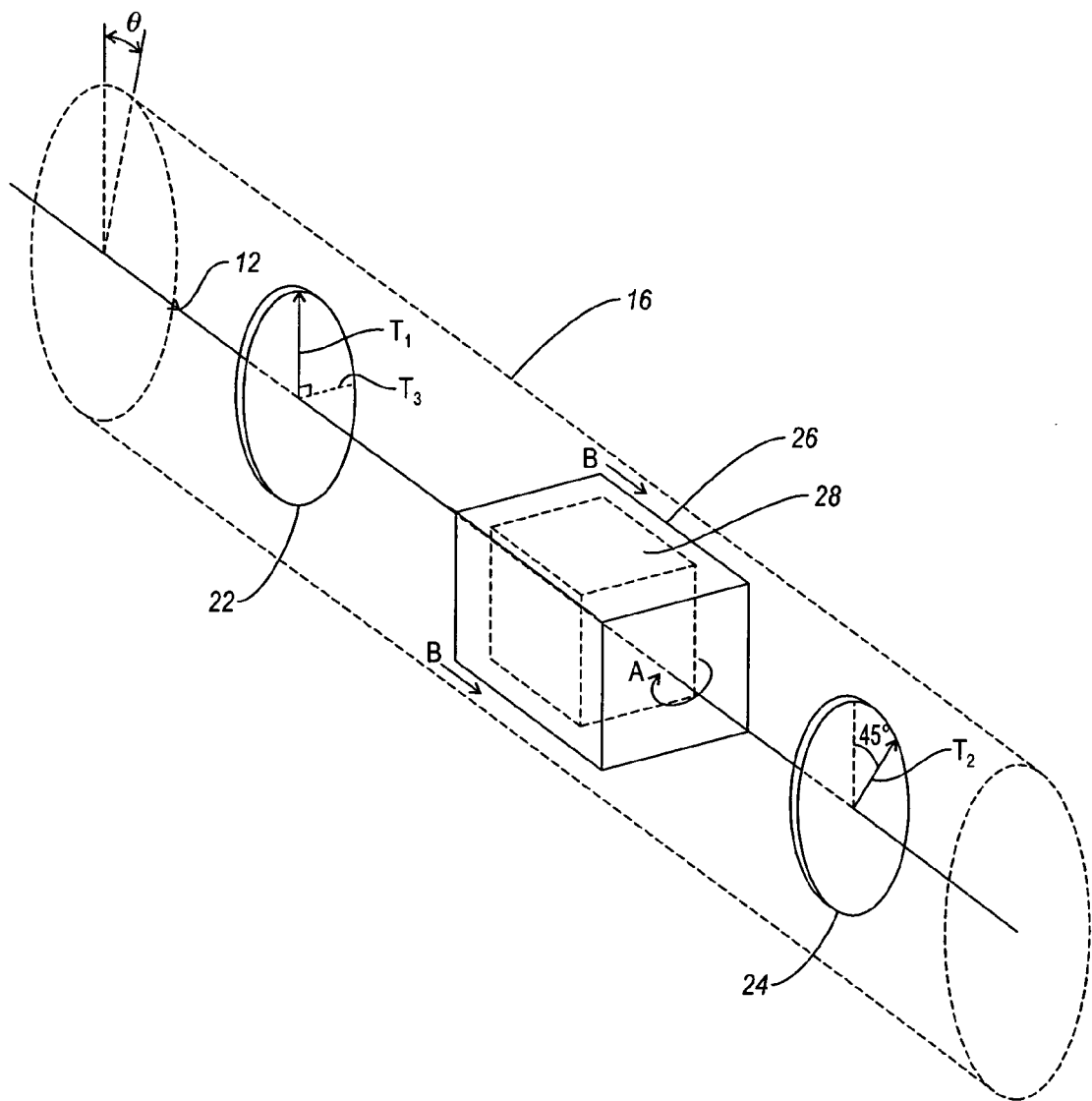
FIG. 2 is a perspective view of the optical isolator in FIG. 1.

FIG. 2 depicts the polarization rotations involved in the variable optical attenuation device of FIG. 1. The optical beam 12 that is polarized along the direction $T_1$ passes through the input polarizer 22 and feeds into the garnet crystal 26. The garnet crystal 26 rotates the optical beam 12 by approximately 45° in the direction A so that the optical beam 12 is polarized in the direction $T_2$. Since the output polarizer 24 transmits light polarized along the direction $T_2$, substantially all of the optical beam 12 passes through the output polarizer 24 and is coupled into an optical fiber (not shown). If any part of the optical beam 12 is back-reflected, substantially all of this back-reflected light also passes through the output polarizer 24 toward the garnet crystal 26 since reflection does not significantly affect the polarization state. However, because the garnet crystal 26 again rotates the back-reflected light by 45° along the direction A, the back-reflected light is polarized in the direction $T_3$ when it exits the garnet crystal 26. Since the input polarizer 22 only transmits light that is polarized in the $T_1$ direction and $T_3$ is orthogonal to $T_1$, the back-reflected light passing through the input polarizer 22 is greatly reduced, limited by the extinction ratio of the polarizer 24.

The variable optical attenuation system 8 can be used to continuously adjust the power of the optical beam 12 by rotating the optical isolator 16 relative to the laser diode 10 about the optical axis. The power is maximized (i.e., attenuation is minimized) when the polarization state D of the optical beam 12 is aligned with the direction $T_1$ of the input polarizer 22. Attenuation is achieved as the optical isolator 16 is rotated by an angle θ, wherein the angle θ is the angle between the polarization state of the optical beam 12 and the direction of maximum transmission $T_1$ of the input polarizer 22. It should be noted that the optical isolator 16 could be fixed, and the diode laser 10 can be rotated. As θ is gradually increased from 0 to 90 degrees, the input polarizer gradually absorbs more of the optical beam 12, increasing the amount of attenuation that is achieved. The portion of optical beam 12 that is transmitted through input polarizer 22 is polarization rotated by garnet crystal 26 and transmitted by output polarizer 24 as described above.

Figure 3:
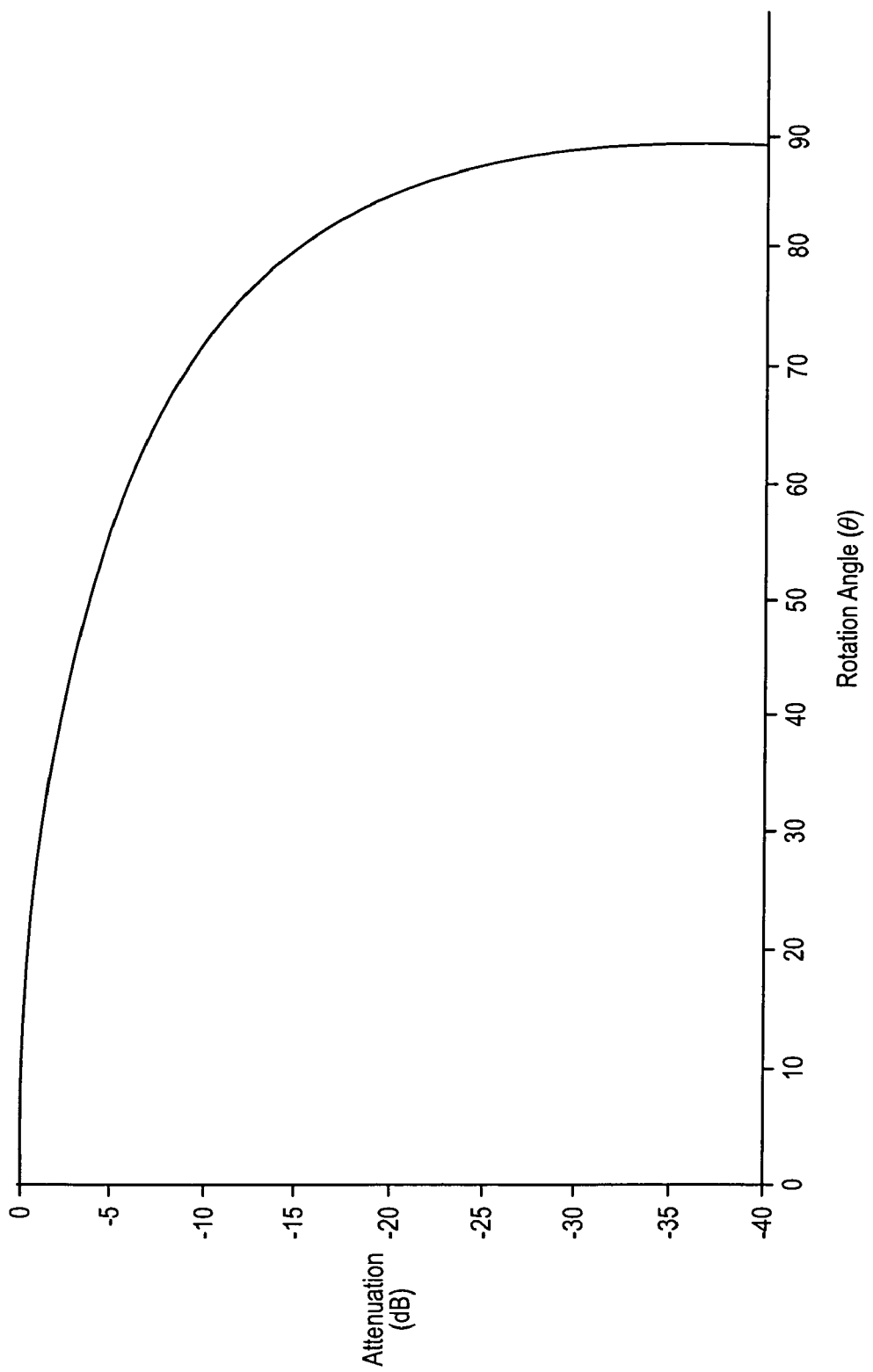
FIG. 3 is a graph showing the attenuation of the optical isolator as a function of rotation angle θ.

FIG. 3 depicts the amount of attenuation that is achieved as a function of angle θ. The intensity I(θ) of the optical beam 12 that is transmitted by the optical isolator 16 as a function of the rotation angle θ is:

$$I(\theta) = I_0 \cdot \cos^2 \theta$$

wherein $I_0$ is the light intensity incident upon the optical isolator 16. As shown in FIG. 3, maximum transmitted power occurs where θ is zero. As θ is increased from zero to 90 degrees, the light intensity I(θ) of optical beam 12 transmitted by the optical isolator 16 drops to nearly zero. The power can be reduced up to the maximum isolation of the device, typically 40 dB or 10000×. Thus, by rotating the isolator from zero to 90 degrees, effectively any signal intensity up to $I_0$ can be obtained. It should be noted that regardless of the rotation angle θ, generally all of the back reflected light is still absorbed by optical isolator 16.

The rotation angle θ can be set in several ways. For example, the laser diode current can be set to provide the desired bandwidth performance, and then the rotation angle θ can be adjusted while the power entering or exiting the optical fiber 18 is actively measured until the desired power intensity is produced. Alternately, the required rotation angle θ can be calculated using the above equation, depending upon the desired attenuation factor. As an added benefit, the isolation of back-reflected light is improved by the projection factor of $\cos^2 \theta$ when the isolator is rotated.

An optical isolator is often used in TOSAs to avoid optical feedback. The method of obtaining variable attenuation requires no additional optical elements or mechanical parts, but advantageously utilizes this existing optical isolator without modification. Unlike filter plates, which would necessarily only be manufactured at discrete values, the isolator attenuation technique of the present invention can achieve arbitrary attenuation values that can be varied to suit each diode laser. Adjusting the rotation angle θ is a fast and inexpensive manufacturing step, yet makes it possible to precisely control either the output power at a fixed diode laser current, or the operating slope efficiency ($\Delta P/\Delta I$), both of which are critical for many practical applications.

Figure 4:
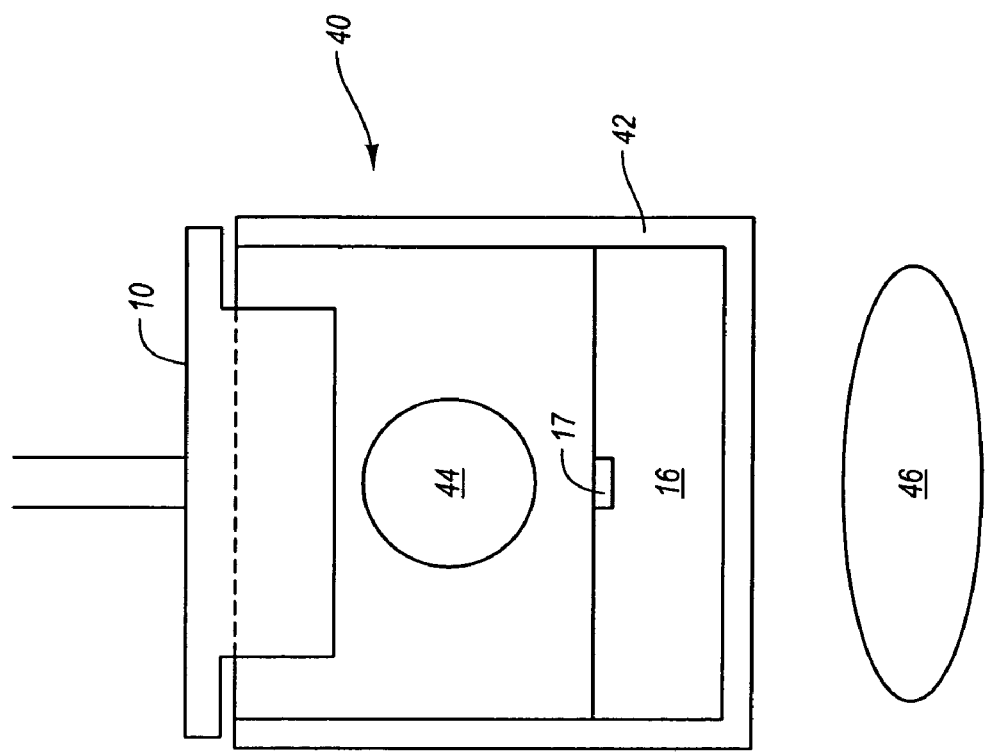
FIG. 4 is a cross sectional view of an optical module built in accordance with the invention.

FIG. 4 depicts a possible implementation of a TOSA 40 in accordance with the invention. The TOSA 40 includes a housing 42 holding the isolator 16 (see FIG. 1), a lens 44, and part of the diode laser 10 (see FIG. 1). The isolator 16 is press-fit or glued into the housing 42 at an arbitrary angular orientation. Although not clearly shown, the isolator 16 has a groove 17 that runs across a surface, indicating its input polarization axis. The lens 44 is securely fixed near the isolator 16 by any conventional mechanical means. The laser diode 10 is inserted into the housing 42 such that the diode laser 10 can still be rotated.

The housing 42 and/or the isolator 16 are rotated relative to the diode laser 10 until the desired power level is achieved. The housing 42, for example, may be rotated by being placed on a motorized or manual rotation stage. A large-area detector power-meter 46 may be positioned near the output of the TOSA 40 to measure or characterize the transmitted power. The isolator orientation can be determined experimentally by maximizing transmission, minimizing transmission and rotating by 90°, or choosing an angle between two transmission minima. This method is advantageous in that it avoids problems due to light "clipping" on the isolator, which is not at its final position during the adjustment. Alternatively, the isolator orientation can be determined by measuring the transmission power as a function of θ while adjusting θ. The θ adjustment is stopped when the power-meter reading indicates that the desired degree of attenuation is achieved. Once the isolator orientation is known, varying the rotation angle θ (defined above) will attenuate the output by $\cos^2 \theta$.

It is to be understood that the present invention is not limited to the embodiment(s) described above and illustrated herein, but encompasses any and all variations falling within the scope of the appended claims. For example, while the output of the optical isolator 16 is shown focused into an optical fiber 18, the optical beam 12 can be delivered to the intended application directly, or with any other conventional optical delivery system (e.g. mirrors, gratings, lenses, etc.).

What is claimed is:

1. A variable optical attenuation device, the device comprising:
    an optical signal source generating an optical signal that is polarized in an original polarization direction D;
    an optical isolator located to receive the optical signal, wherein the optical isolator includes:
        a first polarizer that transmits only light that is substantially polarized in a first polarizer direction $T_1$;
        a polarization rotator optically coupled to the first polarizer for rotating the optical signal by a predetermined angle; and
        a second polarizer optically coupled to the polarization rotator, the second polarizer transmitting only light that is polarized in a second polarizer direction $T_2$ that is different from the first polarization direction $T_1$;
    means for rotating at least one of the optical isolator and the optical signal source to adjust an angle θ, wherein the angle θ is the angle between the original polarization direction D and the polarizer direction $T_1$; and
    wherein the predetermined angle is equal to the difference between the first polarizer direction $T_1$ and the second polarizer direction $T_2$.

2. The device of claim 1, wherein the predetermined angle is approximately 45°.

3. The device of claim 1, wherein the polarization rotator is a Faraday rotator.

4. The device of claim 1, further comprising a signal transfer medium optically coupled to the optical isolator, the signal transfer medium receiving the optical signal from the optical isolator.

5. The device of claim 4, wherein the signal transfer medium is an optical fiber.

6. The device of claim 4, wherein the signal transfer medium reflects a portion of the optical signal, forming a back-reflected light traveling from the input end toward the optical isolator, and wherein the optical isolator prevents substantially all of the back-reflected light from reaching the optical signal source.

7. The device of claim 6, wherein the optical signal is rotated by approximately 45° in a direction A while propagating toward the signal transfer medium and the back-reflected light is also rotated by approximately 45° in the direction A so that the back-reflected light is polarized in a direction that is substantially orthogonal to the polarization direction $T_1$.

8. The device of claim 4, further comprising a focusing element for focusing the optical signal into the input end of the signal transfer medium.

9. The device of claim 1, wherein the means for rotating allows the angle θ to be adjusted continuously.

10. The device of claim 1, further comprising a module housing holding the optical isolator, wherein the module housing is positioned on a rotating surface that rotates the optical isolator relative to the optical signal source.

11. A method of controlling the intensity of an optical signal, the method comprising:
    adjusting an angle θ, which is the difference between an original polarization direction D of the optical signal and a polarizer direction $T_1$, wherein the optical signal is generated by an optical signal source and the polarizer is located inside an optical isolator; and
    wherein the adjustment comprises rotating at least one of the optical signal source and the optical isolator comprising the steps of:
    obtaining a module housing and placing the optical isolator therein;
    inserting the optical signal source into the module housing such that the module housing is rotatable relative to the optical signal source;
    and determining an orientation of the polarizer direction $T_1$.

12. The method of claim 11 further comprising coupling the optical signal into a signal transfer medium that creates a back-reflected light traveling toward the optical signal source, wherein the optical isolator reduces the amount of back reflected light that reaches the optical signal source.

13. The method of claim 12 further comprising rotating the optical signal and the back-reflected light by a predetermined angle using a Faraday rotator that is a part of the optical isolator.

14. The method of claim 11, wherein determining the orientation of the polarizer direction $T_1$ comprises at least one of:
   maximizing a power level of an output exiting the optical isolator;
   minimizing the power level of the output and rotating the optical isolator by 90° relative to the optical signal source;
   and selecting an angle between two power level minima.

15. The method of claim 11, wherein determining the orientation of the polarizer direction $T_1$ comprises:
   adjusting the angle θ;
   and measuring the transmission power as a function of θ.

16. The method of claim 11 further comprising:
   rotating the optical signal coming out of the polarizer by approximately 45° in a direction A so that most of the optical signal has a polarization direction $T_2$;
   allowing only the portion of the optical signal having the polarization direction $T_2$ to reach a signal transfer medium;
   and rotating the portion of the optical signal that is reflected back toward the optical signal source by approximately 45° in the direction A so that most of the optical signal has a polarization direction that is orthogonal to $T_1$ and are blocked by the polarizer.

17. The method of claim 16, wherein rotating the optical signal and rotating the portion of the optical signal that is reflected back both include using a Faraday rotator.

18. The method of claim 11, wherein the adjustment is done continuously to achieve the desired intensity.

19. An optical transmitter module comprising:
   a module housing;
   an optical signal source generating a light that is substantially polarized in a direction D;
   and an optical isolator located inside the module housing, the optical isolator including a polarizer that transmits only light that is substantially polarized in a polarizer direction $T_1$ and receiving the light generated by the optical signal source, wherein the optical isolator is rotatable to adjust an angle θ between the direction D and the polarizer direction $T_1$ to control a power level of the light exiting the optical isolator.

* * * * *